(12) United States Patent
Wan (10) Patent No.: US 6,199,190 B1
(45) Date of Patent: Mar. 6, 2001

(54) CONVOLUTION DECODING TERMINATED BY AN ERROR DETECTION BLOCK CODE WITH DISTRIBUTED PARITY BITS

(75) Inventor: Yongbing Wan, Irvine, CA (US)

(73) Assignee: Conexant Systems, Inc., Newport Beach, CA (US)

( * ) Notice: Subject to any disclaimer, the term of this patent is extended or adjusted under 35 U.S.C. 154(b) by 0 days.

(21) Appl. No.: 09/021,896

(22) Filed: Feb. 11, 1998

(51) Int. Cl.[7] .......................... H03M 13/23; H03M 13/29
(52) U.S. Cl. ............................................ 714/786; 714/758
(58) Field of Search ................................. 714/755, 758, 714/786, 787, 788

(56) References Cited

U.S. PATENT DOCUMENTS 5,838,267 * 11/1998 Wang et al. ............................ 341/94
5,910,182 * 6/1999 Dent et al. ............................ 714/786

OTHER PUBLICATIONS

Nielsen et al., "Comparative Study of Error Correction Coding Schemes for the GSM Half–Rate Channel", ICASSP '92, pp. II–129 to II–132, Dec. 1992.*
Burkert et al., "Turbo Decoding with Unequal Error Protection Applied to GSM Speech", Globecom '96, pp. 2044–2048, Dec. 1996.*

* cited by examiner

Primary Examiner—Stephen M. Baker
(74) Attorney, Agent, or Firm—Knobbe, Martens, Olson & Bear, LLP.

(57) ABSTRACT

An improved encoding technique improves the error detection provided in conventional communication systems. Traditional encoding systems for communication systems often utilize channel-coding in the form of block-coding and convolutional encoding. Block-coding typically utilizes parity bits for error detection. These parity bits are typically placed as a block at the end of the data frame. The present invention provides an improved encoder and decoder which utilize parity bits placed within the data and spread within the data bits for higher reliability.

1 Claim, 9 Drawing Sheets

CONVOLUTION DECODING TERMINATED BY AN ERROR DETECTION BLOCK CODE WITH DISTRIBUTED PARITY BITS

BACKGROUND OF THE INVENTION

1. Field of the Invention

The present invention relates to the field of communications systems. More specifically, the present invention relates to improvements in channel-coding.

2. Brief Description of the Related Art

In communication systems, researchers and developers have sought ways to protect transmitted data from loss during transmission. One method of protecting transmitted data is channel-coding. Channel-coding involves adding redundant bits to the original data so that the receiver of a noisy or disruptive channel can detect and correct bit errors caused by the channel. Further detail is described in Siegmund M. Redl, et al., *An Introduction to GSM,* 110, 113 (1995). Two general methods of channel-coding are discussed in this description: block-coding and convolutional coding.

In block-coding, parity bits are added to the end of the data bits to be transmitted. Parity bits are used to check whether the data bits received contain errors. The number of parity bits added depends on the desired level of error-detection. Convolutional coding, as well understood in the art, involves applying a function to incoming bits to provide additional bits for transmission. Convolutional encoding allows for the proper reconstruction of the data stream at the receiving end, even though some bits may be corrupted during transmission.

When channel-coded data is received, the coded data must be decoded. Decoding processes that use the Viterbi algorithm rely upon the proper identification of the terminating state of the convolutional encoding. The failure to correctly identify the terminating state results in an improper decoding, and an improper data bit stream. The terminating state can be pre-defined by adding predefined tail bits to the bit stream before convolutional coding. This is a popular method in communication systems, and particularly in wireless systems, because the terminating state is known. The tail bits, however, are overhead to the communication system because the tail bits use bandwidth and do not provide error detection or correction.

Communication system designs attempt to reduce overhead, save bandwidth, improve efficiency, and improve the information bit rate. Due to the restricted transmission capacity allocated to communications systems, minimizing the number of bits needed for transmission is desirable. Tail bits, however, reduce the capacity of the system.

This efficiency loss is even greater when the number of information bits in a transmitted package is small, such as in voice data transmissions. For example, if there are 100 data bits and 3 tail bits to be transmitted, the percent of overhead is $3/103$ or roughly 3%—small overhead. But if there are 10 data bits and 3 tail bits to be transmitted, the percent of overhead is $3/13$ or roughly 23.1%—large overhead.

Sometimes, parity bits (an error detection code) are placed at the end of the information burst. Because the parity bits vary with each frame, the terminating state is not pre-defined as with the use of tail bits. Accordingly, the terminating state of the convolutional decoder is determined by using a number of trials, as well known in the art.

Accordingly, the use of parity bits is not, however, error free. Because the parity bits are limited in number, different data streams can result in the same parity bits. False PASS indications can result from the error detection process. The major cause of false PASS indications from the error detection process is the wide range that the parity bits vary with different trials of the terminating state. The greater the range that the parity bits may vary, the larger the probability of a false PASS detection. The large probability of false PASS detection can severely degrade the quality of communication service, such as degraded voice quality.

SUMMARY OF THE INVENTION

The inventors recognized a need to reduce the false PASS indications and to do so without increasing the number of bits transmitted. The present invention is an elegant approach which reduces the probability of false PASS detection while maintaining the performance of convolutional decoding that uses error detection (parity bits). In one embodiment of the invention, the parity or other error check bits are spread through the information burst, instead of being placed at the end of the burst. The combined data/parity frames are then convolutional encoded.

One aspect of the present invention involves a method of coding data, the method comprising the step of coding a sequence of data bits with parity bits to form an information block having a plurality of bits, wherein the parity bits are distributed in groups of one or more parity bits among the data bits.

In one embodiment, the method further involves convolutionally coding the information block to generate a coded information block. The method may also include the step of transmitting the coded information block over a communication channel. The communication channel may be a wireless communication channel, such as a GSM channel or other wireless communication channel.

In another embodiment, the communication channel is a wireline communication channel.

In yet another embodiment, the method further involves the steps of receiving the coded information block at a receiver, convolutionally decoding the coded information block, accumulating the parity bits, and checking the decoded data for errors based upon the parity bits. The parity bits may be distributed at fixed intervals among the data bits. In one embodiment, the fixed intervals begin after a majority of the data bits.

Another aspect of the present invention involves an error detecting decoder responsive to a coded information bit stream having error detection codes distributed within the coded information bit stream, the error detecting decoder comprises a reverse convolutional coding module, the reverse convolutional coding module having an error code assembly module which selects bits that are distributed in the coded information bit stream and provides the error detection code and a decoded information bit stream, and a reverse block coding module coupled to the reverse convolutional coding module and responsive to the error detection code to check for errors in the decoded information bit stream.

In one embodiment, the error detection code comprises parity bits. Advantageously, the parity bits are distributed evenly within the coded information stream.

Yet another aspect of the present invention involves a channel-encoder responsive to an input information bit stream. The channel-encoder has a block-coding module, the block-coding module responsive to the input information bit stream to calculate an error check code, and an error check code distribution module coupled to the block coding module, the error check code distribution module configured to distribute the error check code within the input information bit stream to generate a block-coded information bit stream.

In one embodiment, the channel coder further has a convolutional encoder, the convolutional encoder coupled to the error code distribution module and responsive to the block-coded information bit stream to generate a convolutional encoded information bit stream.

DETAILED DESCRIPTION OF THE INVENTION

The present invention is illustrated in the context of a wireless communication system such as a GSM system (Global System for Mobile Communications). However, this system is chosen merely as exemplary. As apparent from the description, the present invention is applicable in any communication system that transmits data.

Figure 1:
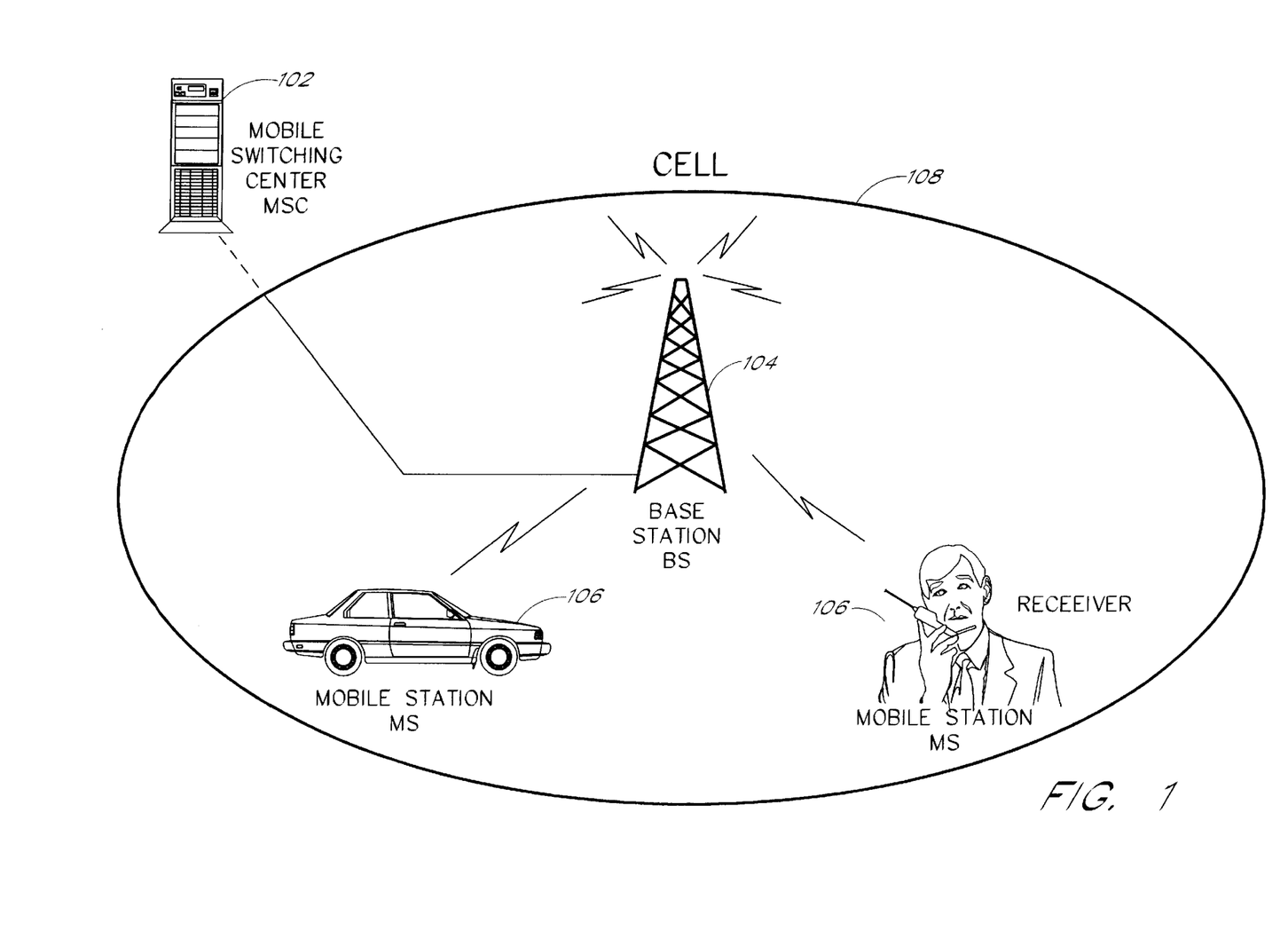
FIG. 1 illustrates components of an exemplary wireless communication system.

FIG. 1 illustrates components of a conventional wireless communication system. A mobile switching center (MSC) 102 communicates with a base station (BS) 104. The base station 104 broadcasts data to and receives data from mobile stations 106 within a cell 108. The cell 108 is a geographic region, roughly hexagonal, having a radius of about 35 kilometers or possibly more.

A mobile station 106 is capable of receiving data from and transmitting data to a base station 104 in compliance with the standard, such as GSM. The standard typically permits mobile users of wireless communication devices to exchange data over a telephone system wherein radio signals carry data to and from the wireless devices.

Typically, additional cells adjacent to the cell 108 permit mobile stations 106 to cross cell boundaries without interrupting communications. The mobile switching center 102 coordinates all communication to and from mobile stations in a multi-cell region.

Mobile stations 106 may move about freely within the cell 108 while communicating either voice or data to other, perhaps fixed, telephone users. Mobile stations not in active communication with other telephone system users may, nevertheless, scan base station 104 transmissions in the cell 108 to detect any telephone calls or pages directed to the mobile station 106.

One example of such a mobile station 106 is a cellular telephone used by a pedestrian who, expecting a telephone call, powers on the cellular telephone while walking in the cell 108. The cellular telephone scans certain frequencies (frequencies known to be used by the standard) to synchronize communication with the base station 104. The cellular telephone then registers with the mobile switching center 102 to make itself known as an active user within the network. The cellular telephone scans data frames broadcast by the base station 104 to detect any telephone calls or pages directed to the cellular telephone. In this call detection mode, the cellular telephone receives, stores and examines paging channel data, and determines whether the data contains a mobile station identifier matching an identifier of the cellular telephone. If a match is detected, the cellular telephone engages in a call establishment communication with the mobile switching center 102 via the base station 104. If no match is detected, the cellular telephone enters an idle state for a predetermined period of time, then exits the idle state to receive another transmission of paging channel data.

Figure 2:
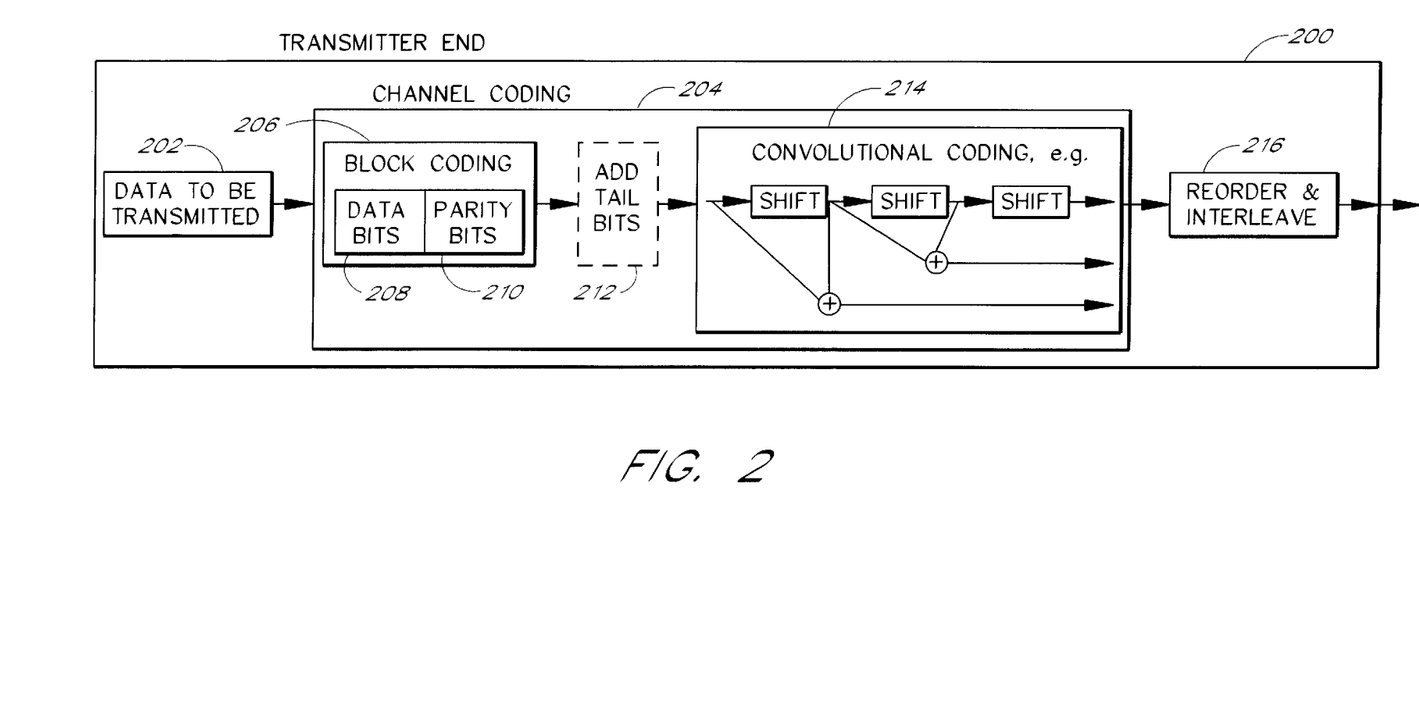
FIG. 2 illustrates a known process of coding data for transmission.

Advantageously, all communications are encoded to promote a lower error rate. FIG. 2 illustrates an exemplary transmission coding process. The data bits 202 to be transmitted may contain voice, other user data, signalling data or control data used to set up and facilitate transmission between the mobile station 106 and the base station 104. The data bits 202 are encoded and then reordered and interleaved.

For the embodiment depicted in FIG. 2, the data to be transmitted 202 is provided to the channel-coding module 204 which provides the coded data to the reorder and interleave module 216. The channel-coding module 204 includes a block-coding module 206, a convolutional coding module 214, and possibly an optional tail bits module 212. If block-coding is used, parity bits 210 are added to the data bits 208 in the embodiment depicted. The resulting data is transmitted from transmitter 200. As explained above, this encoding scheme is not limited to wireless communications. The channel-coding method is described further below.

BLOCK-CODING

As briefly explained above, block-coding involves applying a function to the data bits 208 to generate parity bits 210. The use of the parity bits 210 allows for error detection at the receiving end, as well understood in the art. As explained above, in a conventional system, the parity bits 210 are placed in sequence at the end of the data bits 208 prior to the convolutional coding process. Tail bits may also be added to the data stream to provide for a known terminating state.

CONVOLUTIONAL ENCODING

A convolutional encoder 214 encodes information symbols based upon the present input symbol and the state of the encoder. The present state of the encoder is determined by the symbols which previously entered the encoder. That is, the encoded symbol is a function of the present input symbol and also symbols that entered the encoder before the present input symbol.

Convolutional encoding is typically implemented by shift registers and summers or by look-up tables. The next state and the output of the encoder are functions of the present state of the register or look-up table (i.e., the value of the bits presently stored within the register or look-up table memory), and the input to the register or look-up table.

Figure 3A:
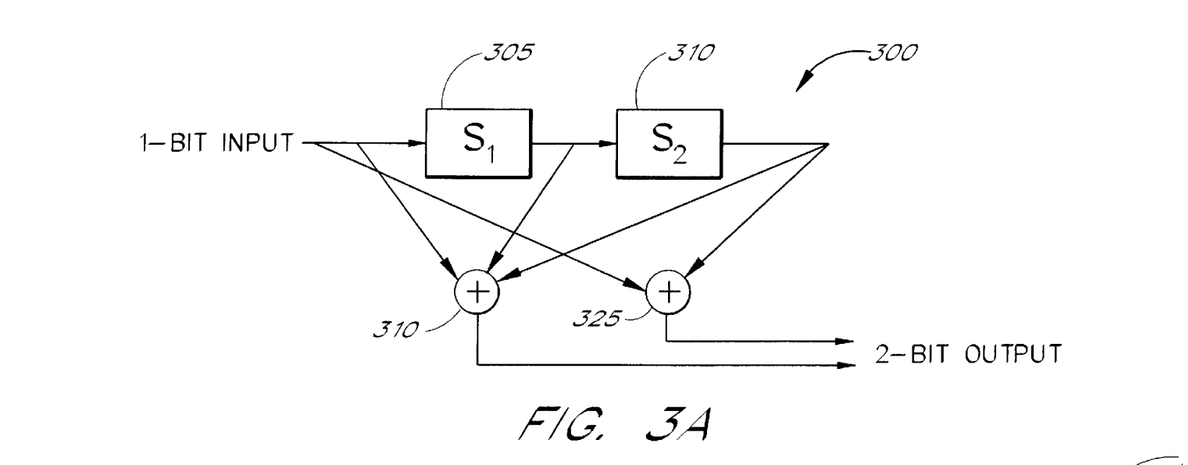
FIG. 3A illustrates an example of a convolutional encoder circuit.
Figure 3B:
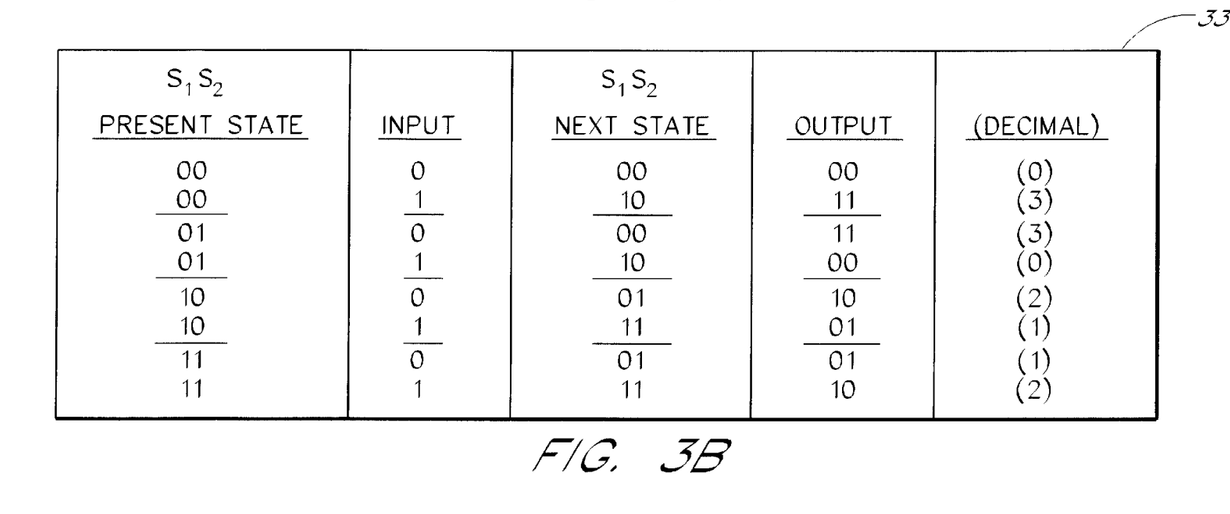
FIG. 3B illustrates a state table describing the operation of the convolutional encoder of FIG. 3A.

FIGS. 3A and 3B illustrate an exemplary embodiment of a convolutional encoder implemented via shift registers and the corresponding state table 330. The encoder 300 as shown in FIG. 3A is merely exemplary to illustrate the operation and implementation of a convolutional encoder. The encoder 300 includes shift register memory units 305 and 310 as well as summers 320 and 325. A one-bit input is encoded into a two-bit output to provide a ½ rate of encoding.

For example, with an initial state of 00 (i.e., the register units 305 and 310 contain bit values of 0, 0 respectively), and an input value of 0, the next state of the encoder 300 is 00 (a zero bit value shifts in while a zero value shifts out). Consequently, the value of the two bits at the output is 00. This is represented in the first line of the state table 330 in FIG. 3B. Thus, when moving from state to state, the encoder 300 is considered to have four possible present states and four possible next states, each two-bit values.

As another example, with the encoder 300 in the present state 10 (i.e., the two registers contain 1,0), an input of 1 will move the encoder 300 to a next state of 11 (i.e., the two registers contain 1,1) and generate an output of 01 (decimal 1). This process is repeated as each successive bit enters the encoder 300 so that the state table 330 can be constructed which shows the possible state transitions of the encoder 300 with the accompanying input and output values which correspond to those transitions.

Figure 4:
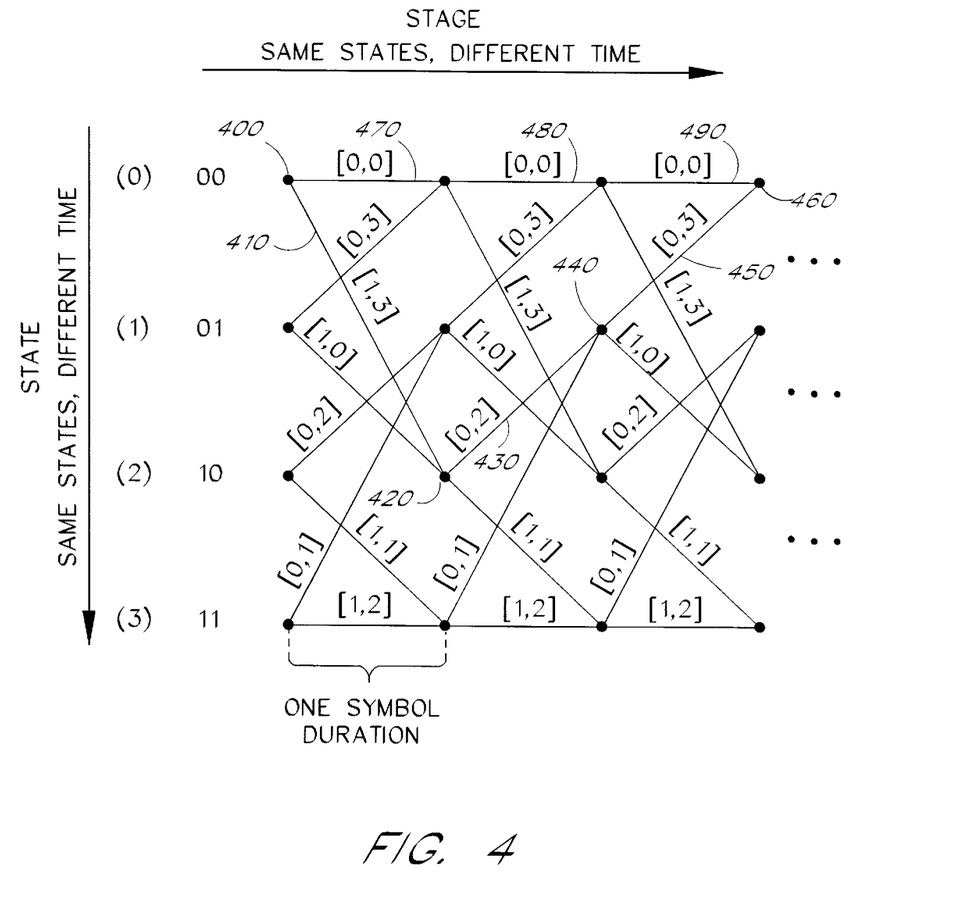
FIG. 4 illustrates a trellis state transition diagram of the convolutional encoder of FIG. 3A.

FIG. 4 is a state transition diagram which indicates the possible state transitions of the encoder 300 of FIG. 3A, along with the input and output values corresponding to the possible transitions. Such diagrams are often called trellis diagrams, hence the name "trellis coding." Each dot on the trellis diagram of FIG. 4 represents a state of the encoder 300. Dots in the same horizontal row correspond to the same state at different times. Dots in the same vertical column represent different states at the same time (i.e., within the duration of the same symbol). Branches between the dots represent possible state transition paths. Thus, for example, there is a branch between the state 01 and the state 00 which indicates that, given the appropriate input, the encoder 300 could go from state 01 to state 00. Because there is no direct branch between states 01 and 11, nor is there a direct branch between the states 01 and 01, it is not possible for the encoder 300 to go from state 01 to either of the states 11 or 01 within one symbol duration.

The number pair along each of the branches depicted in FIG. 4 indicate the [input, output] values which correspond to a given branch. The first number represents the input which causes the transition, while the second number represents the output value resultant upon this transition. For simplicity, these numbers are shown in decimal representations of binary input and output valves.

As seen from the trellis diagram of FIG. 4, the possible state transitions for the encoder 300 are the same for each successive symbol. Thus, the same pattern repeats over and over again for each symbol duration.

As an example, with the encoder 300 in the state 0 (binary 00), represented by a dot 400 in FIG. 4. Upon application of an input value 1 to the encoder 300, the encoder 300 goes from state 0 to state 2 (binary 10), represented by a dot 420, via a path 410. The encoder 300 outputs a value 3 (binary 11). If the value of the next bit applied to the input is 0, then the encoder 300 transitions from state 2 to state 1, represented by a dot 440, via a path 430, while the output of the encoder 300 assumes a value of 2. Finally, upon application of an input bit of 0, the encoder 300 moves from the state 1 to the state 0, represented by a dot 460, via a path 450. Upon entering state 0, the encoder 300 outputs a value 3. Thus, in the foregoing example, input bits 1-0-0 are encoded by the encoder 300 into output bits 11-10-11.

Figure 6:
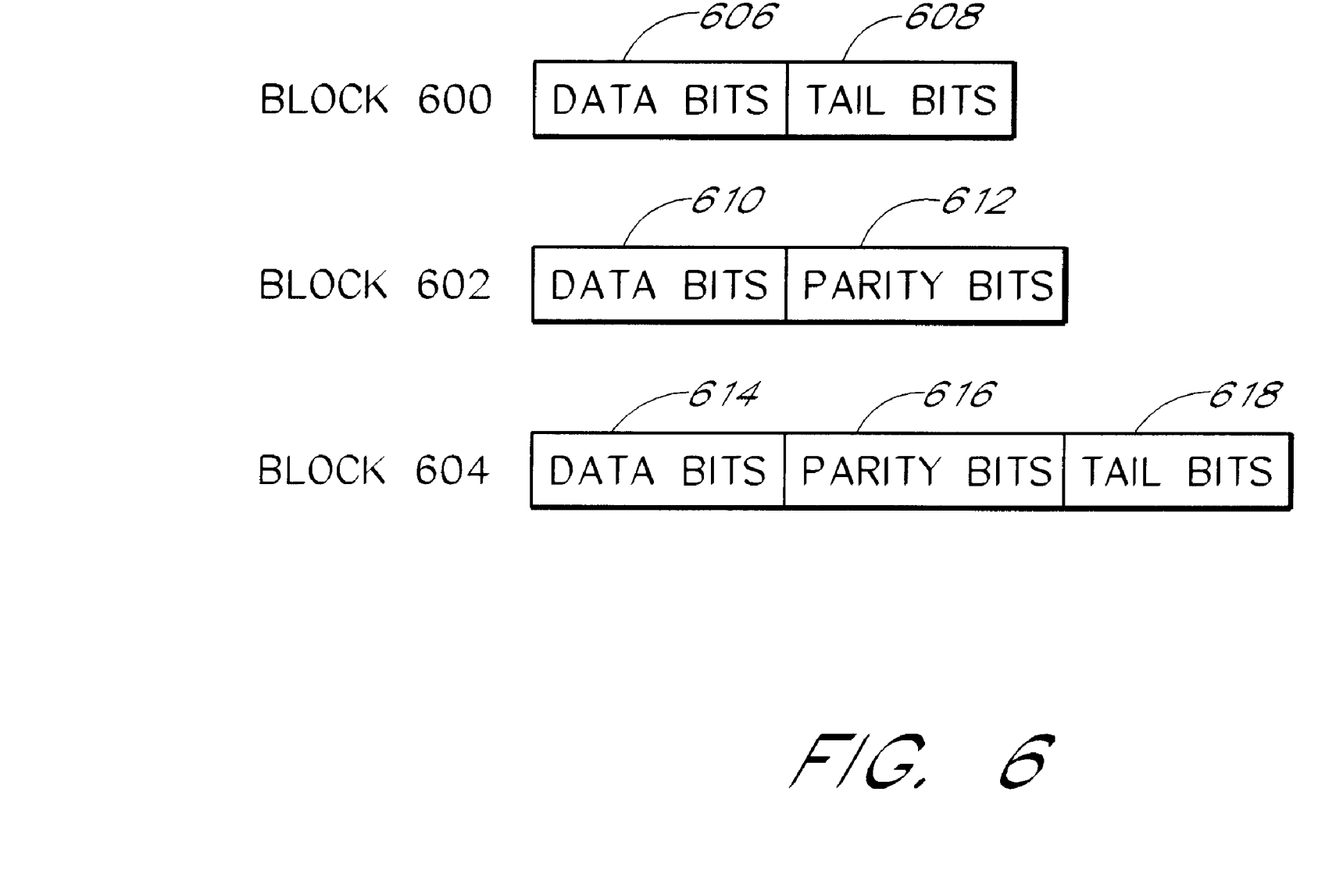
FIG. 6 illustrates configurations of coded bits.

FIG. 6 illustrates some examples of coded bit configurations. In block 600, tail bits 608 are added to the data bits 606. These tail bits 608 are added to the end of each frame. In block 602, parity bits 612 are added to the end of the data bits 610 after block coding of the data bits 610. In block 604, the parity bits 616 are added at the end of the data bits 614 and the tail bits 618 are placed at the end of the parity bits 616.

DECODING IN GENERAL

Figure 5:
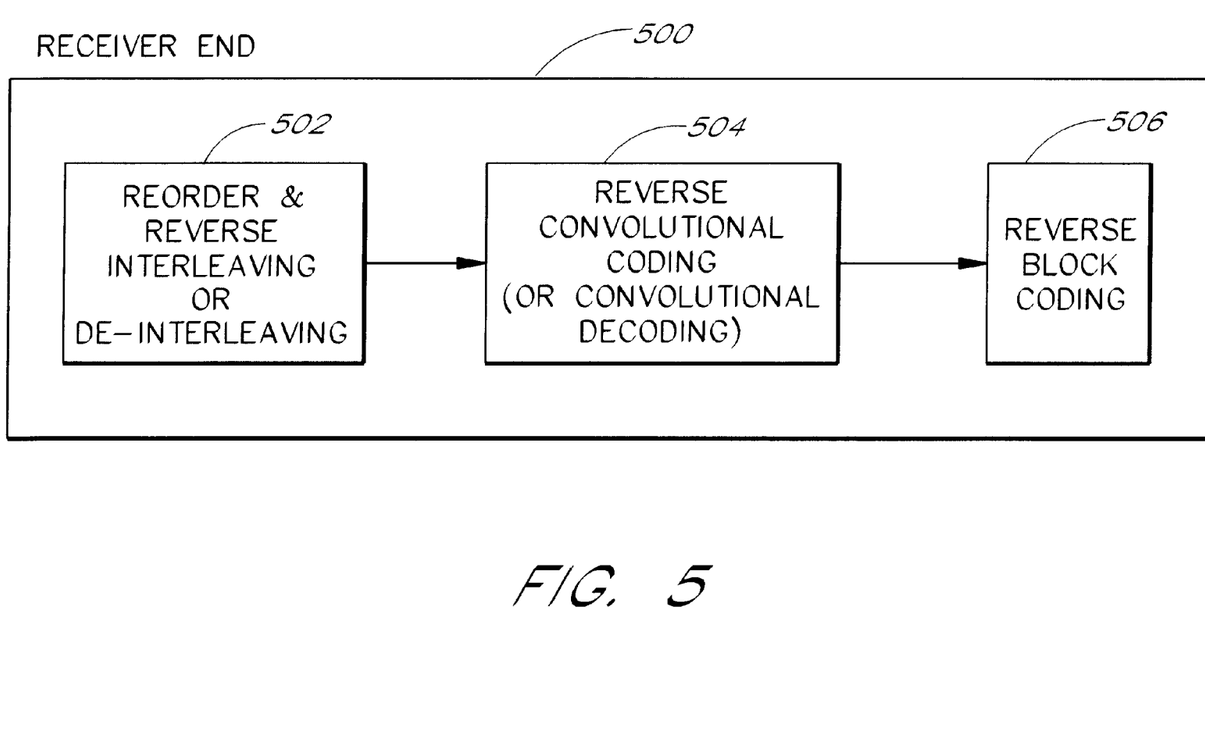
FIG. 5 illustrates the process of decoding data information for reception.

FIG. 5 illustrates a decoder module 500 at the receiving end corresponding to the encoding module 204 of FIG. 2. The received data is reordered, deinterleaved (or reverse interleaved), convolutional decoded (or reverse convolutional coded), and then block decoded (or reverse block-coded). As understood in the art, convolutional decoding attempts to correct errors introduced in the communication channel during transmission. Block decoding is used to determine if there are any errors in the data, after convolutional decoding.

CONVOLUTIONAL DECODING

Convolutional decoding provides for a reduced number of errors at the receiver. For example, assume that a three-bit data stream 1-0-0 is encoded as 11-10-11. Also suppose that the receiver detects the transmitted signal erroneously as 11-11-11. However, because no valid combination of paths can result in this transmission, some correction will take place. In order to determine the original transmitted data, the decoder performs a maximum likelihood decision based upon the possible state transition paths which the encoder 300 might have taken.

In order to identify the most likely path, the decoder determines the probability that the detected data sequence was produced by a first path, the probability that the detected data sequence was generated by a second path and so forth until a probability has been calculated for each calculated path. The path having the highest probability is then selected as the actual path according to either hard or soft decision methods. Typically, trellis decoding techniques calculate path probabilities based upon either Hamming or Euclidean distances between the detected signal and the signals generated by the possible trellis paths.

Convolutional decoding processes that use the Viterbi algorithm require the identification of the terminating state. The 'terminating state' is the last state of the convolutional encoder. Accordingly, the terminating state is also the last bits in an information burst or frame. The number of bits which make up the terminating state depends upon the depth of the encoder.

The Viterbi algorithm has two stages: (1) error metric calculation; and (2) trace back. In the trellis coding diagram of FIG. 4, each path is associated with a transmitted coded bit. Each state is associated with an accumulated error metric number, as well understood in the art. At each state, the decoder calculates the error metric for each path and compares them. The path with the highest probability is called the 'surviving path,' and the decoder stores this in memory.

As understood in the art, during the decoding process, the decoder picks a terminating state (if tail bits are used, the terminating state is a known state). The decoder then traces back along the surviving paths. From the terminating states and surviving paths, the maximum likelihood path is derived, as well understood in the art.

If tail bits are not used, then at the end of error metric calculation, the terminating state is not a known state. After the decoder calculates the error metric and the end state is received, the decoder uses the accumulated error metric number for each state to select the most likely terminating state. The decoder typically starts from the terminating state with the best accumulated error metric number, as known in the art.

BLOCK-DECODING

After convolutional decoding, the parity bits can be used to check for errors. As is well understood in the art, this is generally performed on a block-by-block basis to correspond to the blocks which are used during encoding to calculate the parity bits. Error can be caused by a wrong path, an incorrect previous bit or an incorrect terminating state (where no tail bits are used). If there is no error in the decoded bits, then the terminating state selected is marked as correct. Decoding is complete.

In the case where no tail bits are used, if some error is present in the decoded bits, then the terminating state selected by the decoder may be incorrect. The decoder then attempts decoding using the terminating state with the second best accumulated error metric. The process repeats, and the decoder determines if error is present after block decoding. If there is still error, then the decoder repeats the process with the next best accumulated error metric. If no terminating state with accompanying paths satisfy the block decoding, then the information burst is deleted. The receiver may send a message back to the transceiver requesting a retransmission of that information burst or the receiver may simply repeat the previous information burst (often the case for speech communication).

Block-decoding is generally not 100% error-free. The error detection precision depends upon the number of parity bits. Because each parity bit adds additional data, the number of parity bits used is a trade-off. Accordingly, the number of bits selected typically allows for different data sequences with the same parity. Accordingly, the decoder may indicate false PASS results. This means that the block-decoding process found no errors in the information burst, when errors are actually present in the burst.

The inventors recognized that this problem is worse when parity bits are used and tail bits are not used. This is because the decoder must select the terminating state based on the data it receives, rather than a known terminating state. In addition to selecting the terminating state, the decoder is also determining the parity bits for that particular information burst. These parity bits are assumed to be correct in block-decoding. For example, if the decoder detects a terminating state of 00, then the decoder has the last two parity bits as 00. The block-decoder will use 00 as the last two parity bits. Because there is only one terminating state that will generate correct parity bits, incorrect parity bits damage the reliability of the block decoder. Thus, if the last symbol to be transmitted happens to be a symbol with errors, then the terminating state is incorrect and the parity bits are incorrect. This results in difficulties in proper convolutional decoding, and in proper error detection. Furthermore, if the parity bits are incorrect, which results in an incorrect terminating state, false PASS indications may result.

Because the terminating state and parity bits are very important to proper decoding and error detection, the present invention addresses a solution to the problems created by having the parity bits at the end of each frame.

DATA AND PARITY BIT CONFIGURATION

Figure 7A:
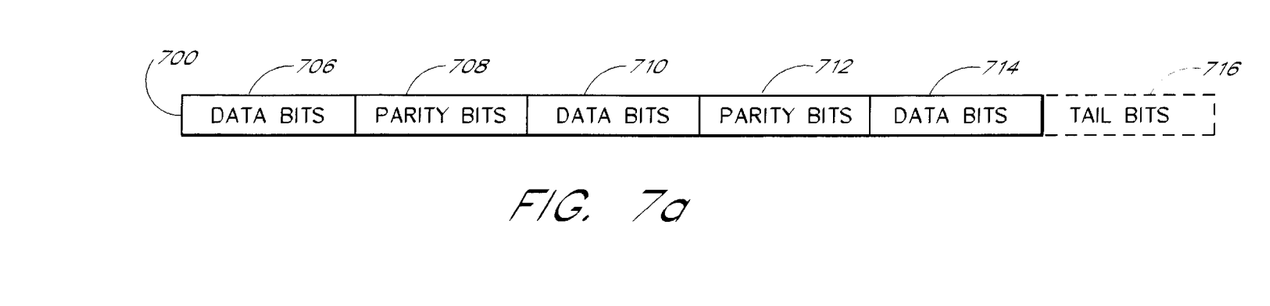
FIGS. 7a–7c illustrate configurations of data and parity bits in accordance with the present invention.
Figure 7B:
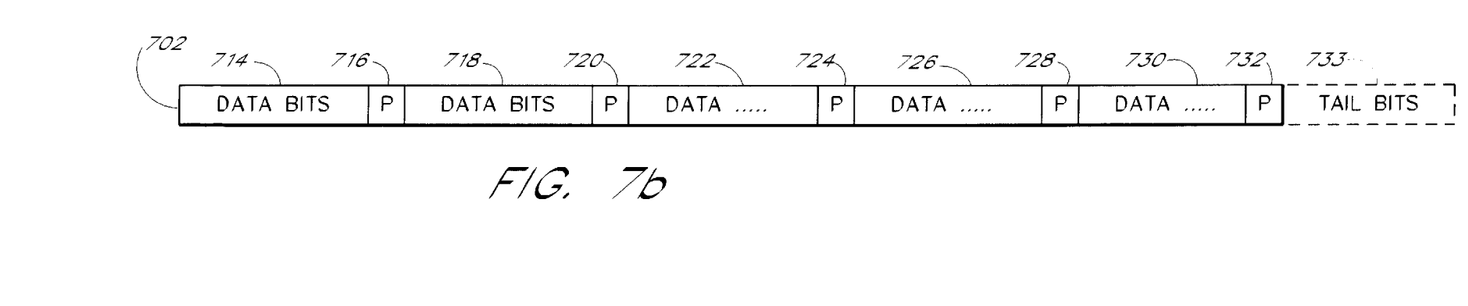
Figure 7C:
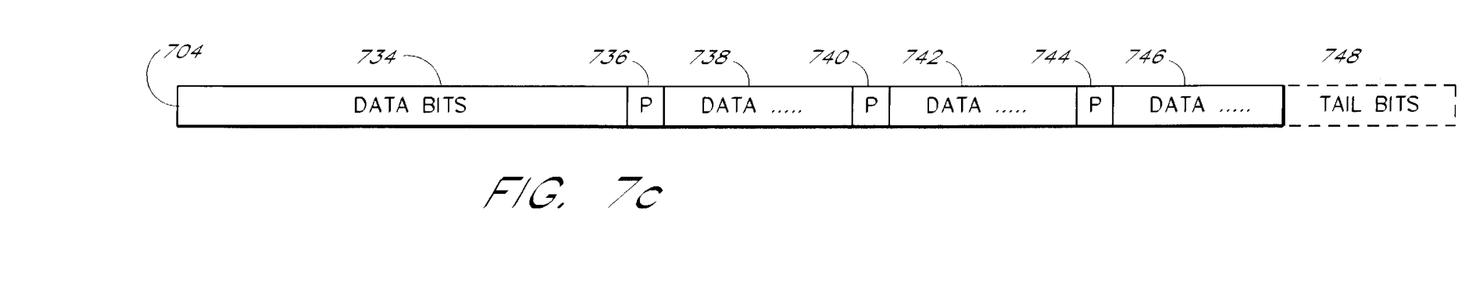

FIGS. 7a–c illustrate various configurations of data bits and parity bits in accordance with the present invention. The present invention involves distributing the parity bits among the data bits rather than at the end of the data bits.

In one embodiment of the invention, the encoder distributes parity bits in blocks of bits. As depicted in FIG. 7a, blocks of parity bits 708, 712 are distributed among data bits 706, 710 and 714. In an optional embodiment, tail bits 716 can be included at the end of the data burst in order to determine the terminating state as a known state.

In another embodiment of the invention, the parity bits may be distributed in single bit increments as depicted in FIGS. 7b and 7c. The parity bits may be distributed according to a pattern such as same number of data bits followed by same number of parity bits or any other pattern of parity bits such that the decoder can pluck the parity bits from the bit stream. As depicted in FIG. 7c, burst 704 is made up of a patterned block: data bits 734 followed parity bit 736, data block 738, parity bit 740, data block 742, parity bit 744 and data block 746. Data blocks 738, 742, and 746 may contain fewer data bits than the first data block 734. In other words, the repeating pattern of parity bits and data blocks may begin after a majority of data bits 734. As in the burst 700 of FIG. 7a, the burst 704 may include optional tail bits 748 for a known terminating state.

FIG. 7b depicts another embodiment of the present invention with parity bits mixed among data bits in burst 702. As depicted in FIG. 7b, one or more (but not all) parity bits 732 may be placed at the end of the data burst 702. Preferably, the number of parity bits placed at the end of an information burst is less than the number of bits which make up the terminating state of the decoder. As with FIGS. 7a and 7c, optional tail bits 733 may be provided at the end of the entire burst in order to have a known terminating state.

Figure 8:
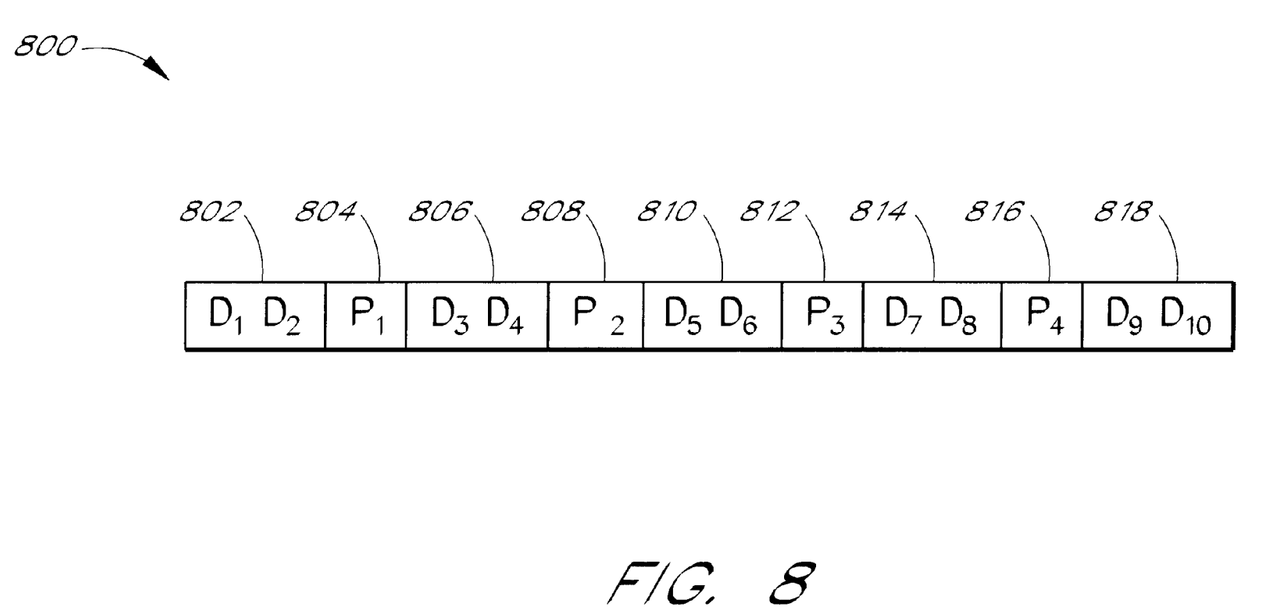
FIG. 8 illustrates an example of a bit configuration in accordance with the present invention.

FIG. 8 illustrates a more detailed example of a bit configuration in accordance with the present invention. The data bits are denoted by 'D' and parity bits are denoted by 'P.' The combined parity bits P1, P2, P3, P4 may be used during block decoding to detect errors in the information burst (D1 . . . D10) 800 after convolutional decoding. The terminating state during convolutional decoding is D9 and D10. Even if the receiver receives incorrect bits for D9 and D10 or the decoder selects the wrong terminating state, error-detection during block-decoding is unaffected. In effect, the parity bits are used to protect the accuracy of the data bits, and the data bits are used to protect the parity bits.

In these configurations, there is less chance that the parity bits will all be in error. The parity bits are part of the transmission data which allows for some correction during the convolutional decoding process. Because the parity bits are distributed in a wide range in the burst, they will change to a less degree with different trials of the terminating state. Thus, the probability of a false PASS result during block decoding is reduced significantly.

Figure 9:
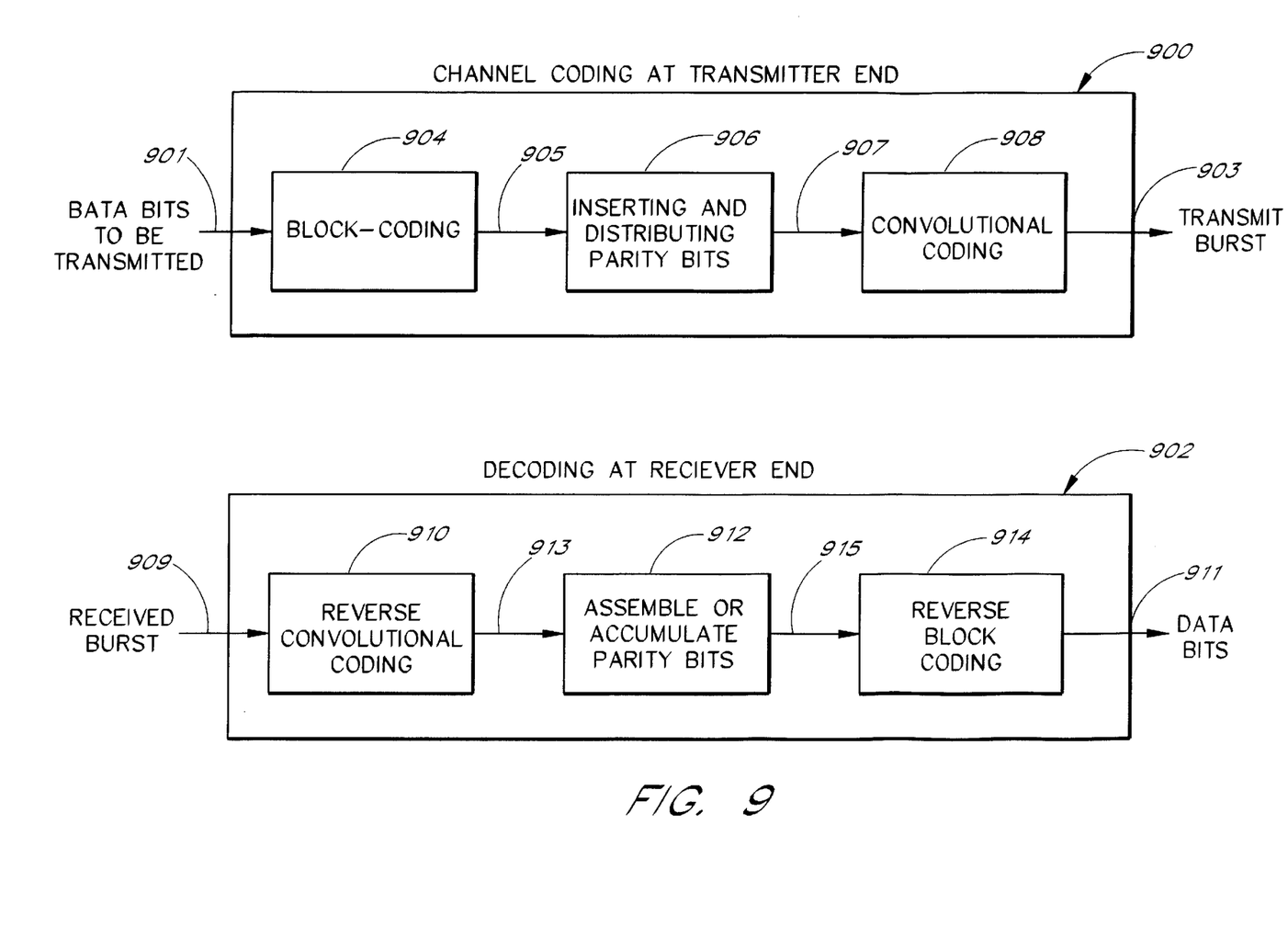
FIG. 9 illustrates an encoder and decoder in accordance with the present invention.

FIG. 9 illustrates a channel coder 900 and a channel decoder 902, in accordance with the present invention. The channel coding module 900 receives data to be transmitted at an input 901 and provides coded bursts at an output 903. The channel coding module 900 has a block coding module 904, a parity bits insertion module 906, and a convolutional coding module 908. Similarly, the decoder module 902 receives the transmitted burst at an input 909 and provides the decoded data bits at an output 911. The decoder 902 has a reverse convolutional coding module 910, a parity bits accumulation module 912, and a reverse block coding module 914.

For the channel coding module 900, the block coding module 904 performs conventional block coding by calculating an error code or error check, as well understood in the art. The parity bit distribution module 906 accepts the data bits input to the block coding module 904 and the resulting parity bits from the block coding module 904 on an output 905, which also forms the input to the parity bit distribution module 906. It should be understood that the output 905 may comprise a signal line for parity bits and a signal line for data bits. The parity bits distribution module 906 responds to this information and distributes the parity bits according to the predefined pattern among the data bits. The resulting data stream is provided by the parity bits distribution module 906 on an output 907 which forms the input to the convolutional coding module 908. The convolutional coding module 908 responds to the data stream from the parity bits distribution module 906 and convolutionally encodes the combined data/parity bit stream. The resulting bit stream is transmitted with any of a number of known modulation and transmission techniques.

With respect to the decoder module 902 at the receiving end, the transmitted burst is demodulated, as well understood in the art, and provided to the decoding module 902 at its input 909. The received data is reversed convolutional coded using an algorithm such as the Viterbi algorithm, as well understood in the art, in a reverse convolutional coding module 910. The resulting data stream is provided to the parity bits accumulation module 912 via at least one signal line 913. The parity bits accumulation module 912 plucks the parity bits from the bit stream and accumulates the parity bits and accumulates the data bits as separate bit streams. The parity bits accumulation module 912 provides the resulting parity bits data stream and the data bits data stream on an output 915, which also forms an input 915 to the reverse block coding module 914. It should be understood that the output 915 may comprise a signal line for parity bits and a signal line for data bits. The reverse block coding module 914 performs the same parity operation as performed in the encoding module 900 and compares the result to the parity bits which have been plucked from the combined stream in the module 912. If the error detection indicates no errors have been found, then the data bits are provided on an output 911 to the decoding module 902. As well understood in the art, various attempts can be made using different terminating states and less than optimal paths in the reverse convolutional coding module 910 to attempt to reconstruct the data in accordance with known techniques.

Although the invention has been described in terms of a preferred embodiment, many variations will come within the scope of the claims. All such variations are intended to be included within the appended claims. The invention may be embodied in other specific forms without departing from the essential characteristics as described herein. The embodiments described above are to be considered in all respects as illustrative only and not restrictive in any manner. The scope of the invention is indicated by the following claims rather than by the foregoing description. Any and all changes which come within the meaning and range of equivalency of the claims are to be considered within their scope.

What is claimed is:

1. A method of coding data, said method comprising the steps of:

blockcoding a sequence of data bits with parity bits to form an information block having a plurality of bits, wherein said parity bits are distributed in groups of one or more parity bits at fixed intervals among the data bits, wherein said fixed intervals begin after a majority of said data bits;

convolutionally coding said information block to generate a coded information block;

transmitting said coded information block over a communication channel;

receiving said coded information block at a receiver;

convolutionally decoding said coded information block;

accumulating the parity bits; and checking the decoded data for errors based upon the parity bits.

\* \* \* \* \*